United States Patent [19]

VandenBerg

[11] Patent Number: Plant 7,500

[45] Date of Patent: Apr. 16, 1991

[54] CHRYSANTHEMUM PLANT NAMED DESIREE

[75] Inventor: Cornelis P. VandenBerg, Salinas, Calif.

[73] Assignee: Yoder Brothers, Inc., Barberton, Ohio

[21] Appl. No.: 435,820

[22] Filed: Nov. 14, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Desiree particularly characterized by its flat capitulum form, daisy capitulum type; light purple ray floret color with a dark red-purple underside of ray florets and dark red-purple flower buds; diameter across face of capitulum of 30 to 32 mm at maturity when grown as a pinched spray pot mum; very floriferous with an excellent display of many small flowers; uniform seven week photoperiodic flowering response to short days; short plant height when grown as a pinched pot mum; small, dark green foliage; spreading and very prolific branching pattern; and excellent tolerance to high temperatures for bud initiation and flower development.

3 Drawing Sheets

1

The present invention comprises a new and distinct cultivar of Chrysanthemum, botanically known as *Dendranthema grandiflora*, and referred to by the cultivar name Desiree.

Desiree, identified as 86-66013, was originated from a cross made by Cornelis P. VandenBerg in a controlled breeding program in Salinas, Calif., in 1986.

The female parent of Desiree was an unnamed seedling identified as 84-X82004 and described as a pink daisy spray pot mum. The male parent of Desiree was an unnamed seedling identified as 83-S01002, and describes as a yellow daisy spray pot mum with many very small flowers.

Desiree was discovered and selected as one flowering plant within the progeny of the stated cross by Cornelis P. VandenBerg in January of 1987, in a controlled environment in Salinas, Calif.

The first act of asexual reproduction of Desiree was accomplished when vegetative cuttings were taken from the initial selection in March ob 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Desiree are firmly fixed and are retained through successive generations of asexual reproduction.

Desiree has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The high temperature tolerance of Desiree as noted below was determined in a controlled environment in Salinas, Calif., where temperatures were maintained at 35 degrees Celsius during the day and 24 degrees Celsius during the night for the duration of the crop.

The following traits have been repeatedly observed and are determined to be basic characteristics of Desiree, which, in combination, distinguish this chrysanthemum as a new and distinct cultivar:

2

1. Flat capitulum form.
2. Daisy capitulum type.
3. Light purple ray floret color with the underside of the ray florets and the flower buds both being dark red-purple.
4. Diameter across face of capitulum of 30 to 32 mm at maturity, when grown as a pinched spray pot mum.
5. Very floriferous with an excellent display of many small flowers.
6. Uniform seven week photoperiodic flowering response to short days.
7. Short plant height, requiring 7 to 14 long days after pinch prior to short days and 1 to 2 applications of 2500 ppm B-9 SP to attain a flowered plant height of 25 to 35 cm for year-round flowerings when grown as a pinched pot mum in a 15 cm pot.
8. Small, dark green foliage.
9. Branching pattern is spreading and very prolific, each plant having 6 to 8 laterals after pinch.
10. Excellent tolerance to high temperatures for bud initiation and flower development.

The accompanying photographic drawings show typical inflorescence and leaf characteristics of Desiree, with the colors being as nearly true as possible with illustrations of this type.

Sheet 1 is a color photograph of Desiree grown as a pinched spray mum in a 15 cm pot.

Sheet 2 is a black and white photograph of three views of the inflorescence of Desiree. Although the photograph is not in clor, the much darker underside of the ray florets will be apparent.

Sheet 3 is a black and white photograph showing the upper and under sides of the leaves of Desiree at three stages of development (mature, intermediate and immature).

No commercial cultivar known to the inventor can be compared with Desiree. The combination of light purple ray flower color with dark red-purple ray floret underside and buds, very high number of small flowers, small dark green foliage, and spreading and very prolific branching is unique, and is not repressented in any commercial pattern cultivar known to the inventor.

In the following description color reference are made to The Royal Horticultural Society Colour Chart. The color values were determined on plant material grown as a pinched spray pot mum in Salinas, Calif. on May 31, 1989.

Classification:

*Botanical.*—*Dendranthema grandiflora* cv Desiree.

*Commercial.*—Daisy spray pot mum.

Inflorescence

A. Capitulum:

*Form.*—Flat.

*Type.*—Daisy.

*Diameter across face.*—From 30 to 32 mm at maturity.

B. Corolla of ray florets:

*Color (general tonality from a distance of three meters).*—Light purple, with dark red-purple underside and buds.

*Color (upper surface).*—75B, fading to 75C to 75D.

*Color (under surface).*—71B.

*Shape.*—Straight, oblong, slightly ribbed.

C. Corolla of disc florets:

*Color (mature).*—12A.

*Color (immature).*—1B.

D. Reproductive organs:

*Androecium.*—Present on disc florets only; scant pollen.

*Gynoecium.*—Present on both ray and disc florets.

Plant

A. General appearance:

*Height.*—Short; 25 to 35 cm as a pinched spray pot mum with 7 to 14 long days after pinch prior to short days and 1 to 2 applications of 2500 ppm B-9 SP, when grown as a pinched pot mum in a 15 cm pot.

*Branching pattern.*—Spreading and very prolific.

B. Foliage:

*Color (upper surface).*—147A.

*Color (under surface).*—147B.

*Shape.*—Small, lobed and slightly serrated.

I claim:

1. A new and distinct Chrysanthemum plant named Desiree, as described and illustrated.

* * * * *

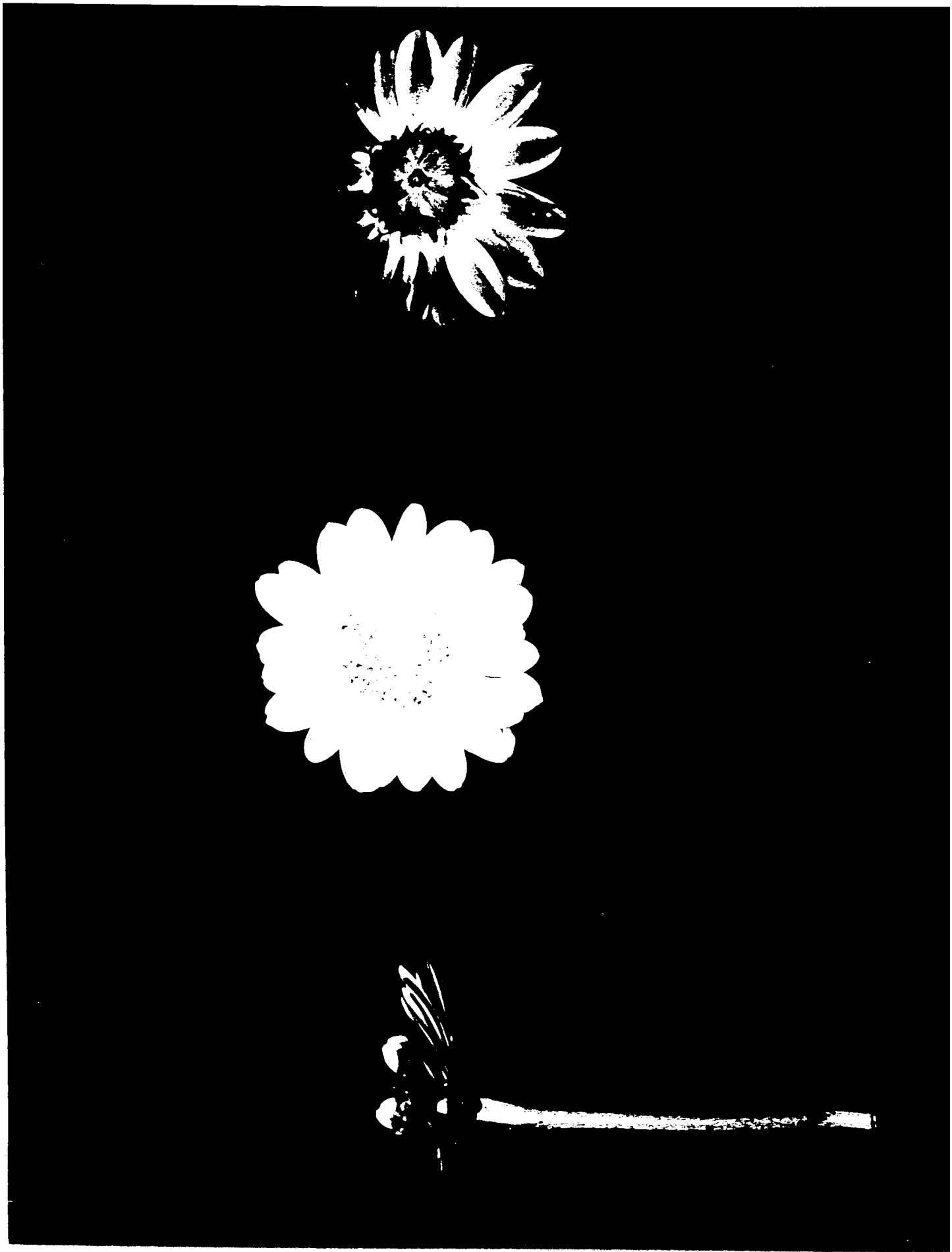

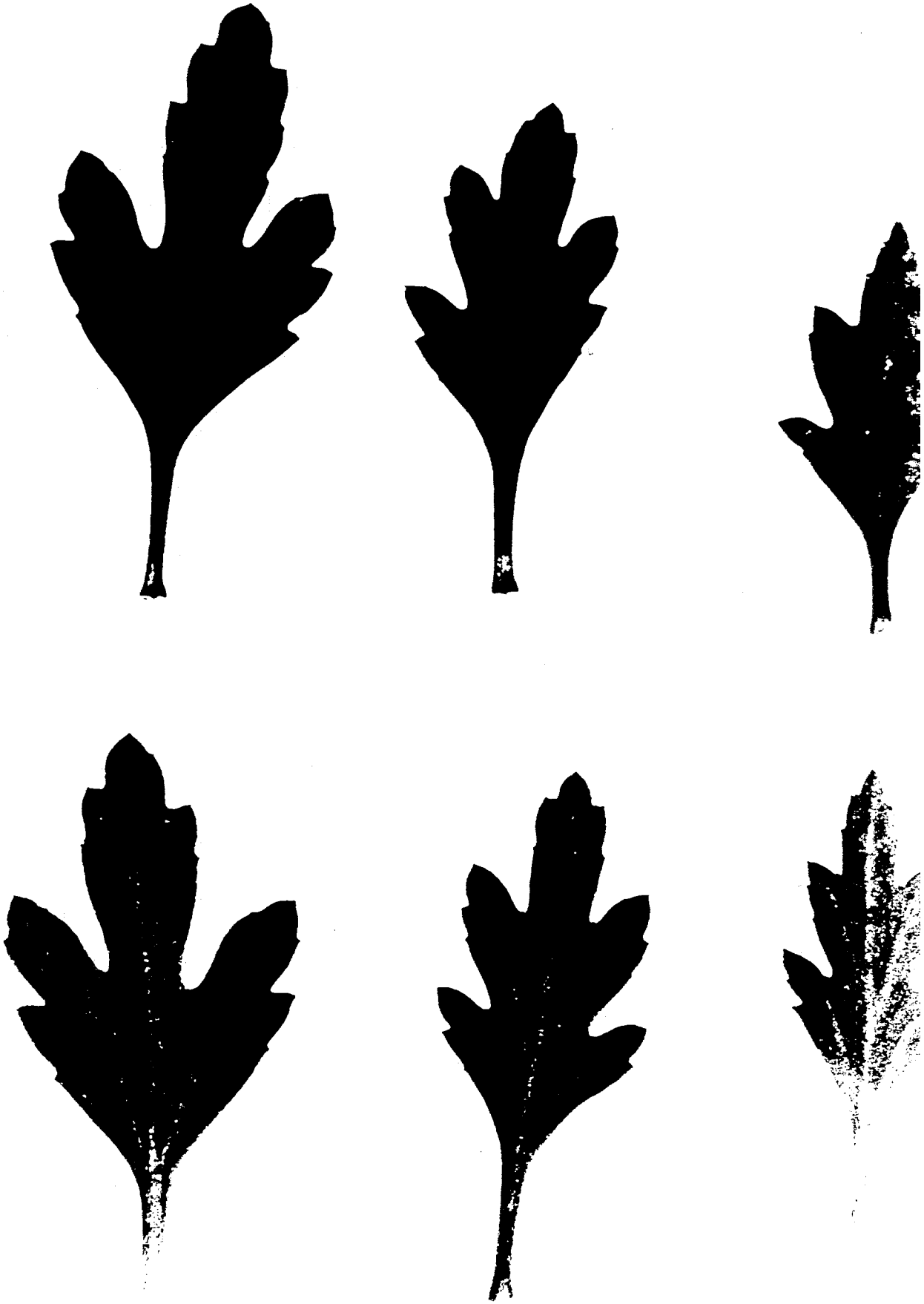

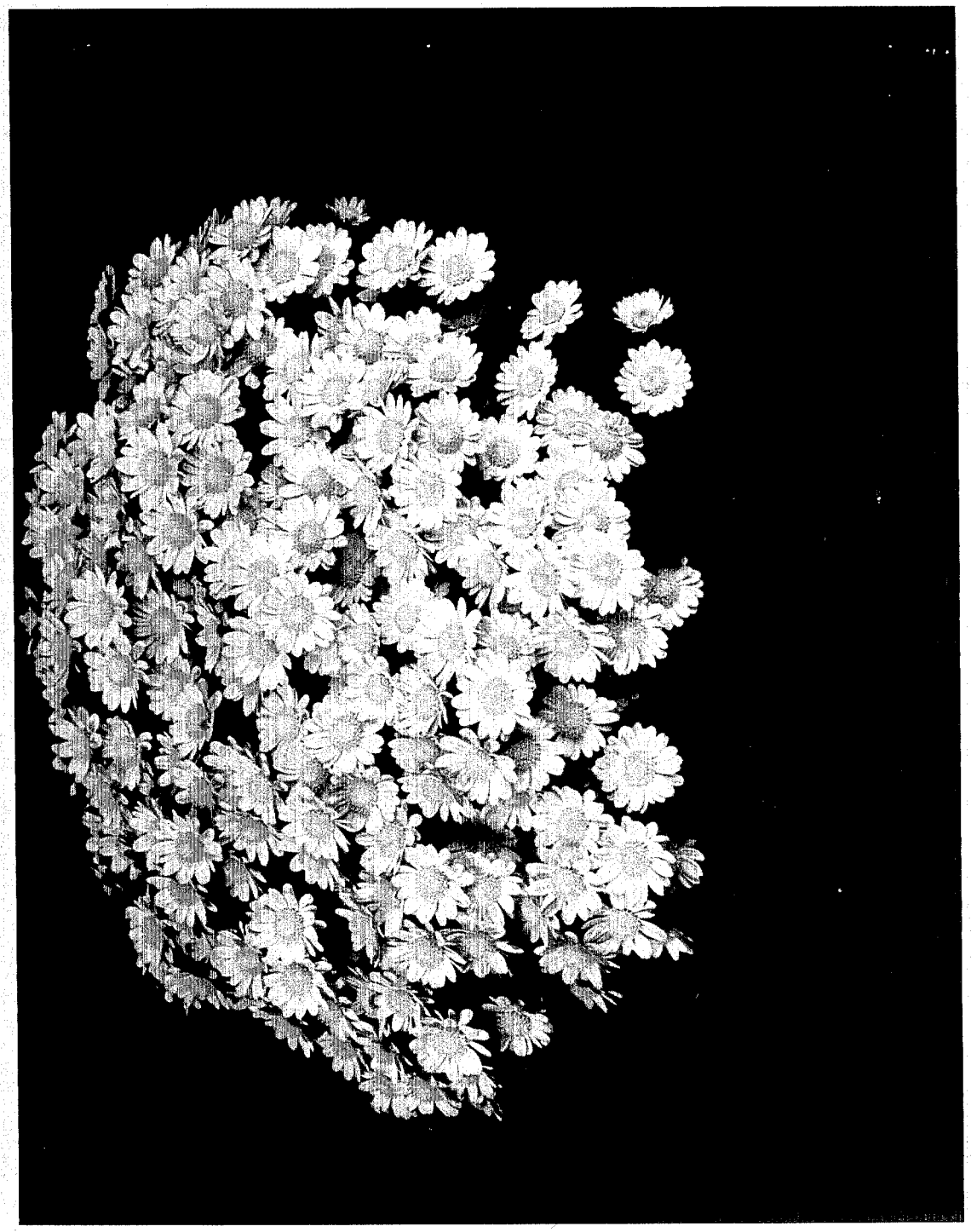

UNITED STATES PATENT AND TRADEMARK OFFICE

CERTIFICATE OF CORRECTION

PATENT NO. : PP 7,500

DATED : April 16, 1991

INVENTOR(S) : Cornelis P. VandenBerg

It is certified that error appears in the above-identified patent and that said Letters Patent is hereby corrected as shown below:

Column 1, line 5, "86-66013" should read --86-666013--.

Column 1, line 20, "March ob" should read --March of--.

Column 3, line 1, "branching is" should read --branching pattern is--.

Column 3, line 1, "repressented" should read --represented--.

Column 3, line 2, "commercial pattern cultivar" should read --commercial cultivar--.

Column 3, line 3, "reference" should read --references--.

Signed and Sealed this

Twenty-third Day of November, 1993

*Attest:*

*Attesting Officer*

Bruce Lehman

BRUCE LEHMAN

*Commissioner of Patents and Trademarks*